US011898274B2

(12) United States Patent
Kosan et al.

(10) Patent No.: US 11,898,274 B2
(45) Date of Patent: Feb. 13, 2024

(54) HYDROGEL-FORMING MULTICOMPONENT FIBER

(71) Applicant: Carl Freudenberg KG, Weinheim (DE)

(72) Inventors: Birgit Kosan, Rudolstadt (DE); Michael Mooz, Saalfeld (DE); Frank Meister, Rudolstadt (DE)

(73) Assignee: CARL FREUDENBERG KG, Weinheim (DE)

( * ) Notice: Subject to any disclaimer, the term of this patent is extended or adjusted under 35 U.S.C. 154(b) by 691 days.

(21) Appl. No.: 16/625,003

(22) PCT Filed: Jun. 21, 2018

(86) PCT No.: PCT/EP2018/066610
§ 371 (c)(1),
(2) Date: Dec. 20, 2019

(87) PCT Pub. No.: WO2019/002095
PCT Pub. Date: Jan. 3, 2019

(65) Prior Publication Data
US 2020/0141031 A1 May 7, 2020

(30) Foreign Application Priority Data
Jun. 27, 2017 (DE) .................... 10 2017 006 025.8

(51) Int. Cl.
*D01F 8/02* (2006.01)
*D01D 1/02* (2006.01)
*D01D 5/06* (2006.01)
*A61L 26/00* (2006.01)
*A61L 17/10* (2006.01)
*A61L 15/28* (2006.01)
*A61L 15/60* (2006.01)

(52) U.S. Cl.
CPC .............. *D01F 8/02* (2013.01); *A61L 15/28* (2013.01); *A61L 15/60* (2013.01); *A61L 17/10* (2013.01); *A61L 26/008* (2013.01); *A61L 26/0023* (2013.01); *D01D 1/02* (2013.01); *D01D 5/06* (2013.01)

(58) Field of Classification Search
CPC . D01F 8/02; A61L 15/28; A61L 15/60; A61L 17/10; A61L 26/0023; A61L 26/008; A61L 15/225

USPC .............................................. 442/362; 514/57
See application file for complete search history.

(56) References Cited

U.S. PATENT DOCUMENTS

| | | | |
|---|---|---|---|
| 4,199,367 A | 4/1980 | Smith | |
| 4,289,824 A | 9/1981 | Smith | |
| 6,548,730 B1 | 4/2003 | Patel et al. | |
| 9,259,506 B2 | 2/2016 | Schmitz et al. | |
| 2005/0101900 A1* | 5/2005 | Qin | A61L 15/18 602/49 |
| 2005/0136253 A1 | 6/2005 | Michael et al. | |
| 2008/0082065 A1 | 4/2008 | Weerawarna | |
| 2014/0227370 A1* | 8/2014 | Miraftab | C08K 3/16 536/3 |
| 2014/0309574 A1 | 10/2014 | Cotton | |
| 2014/0322514 A1 | 10/2014 | Pham et al. | |
| 2016/0121013 A1 | 5/2016 | Ballamy et al. | |

FOREIGN PATENT DOCUMENTS

| | | | |
|---|---|---|---|
| AU | 757461 B | 2/2003 | |
| CN | 103060946 A | 4/2013 | |
| DE | 102012007307 A1 | 10/2013 | |
| EP | 1091770 A1 | 4/2001 | |
| EP | 1849464 A1 | 10/2007 | |
| GB | 2518199 A | 3/2015 | |
| WO | WO 95/19795 * | 7/1995 | ............ A61L 15/28 |
| WO | WO 0001425 A1 | 1/2000 | |

OTHER PUBLICATIONS

Frey, Polymer Reviews, 2008, 48, 378-391.*

* cited by examiner

*Primary Examiner* — Ganapathy Krishnan
(74) *Attorney, Agent, or Firm* — LEYDIG, VOIT & MAYER, LTD.

(57) ABSTRACT

A hydrogel-forming multicomponent fiber includes: at least one first fiber component; and at least one second fiber component. The first and the second fiber components are selected independently of one another from a group consisting of polysaccharides and/or polysaccharide derivatives. The first fiber component is produced from a polysaccharide and/or a polysaccharide derivative having a water solubility of more than 50% by weight. The multicomponent fiber has a water solubility of less than 15% by weight.

18 Claims, 2 Drawing Sheets

HYDROGEL-FORMING MULTICOMPONENT FIBER

CROSS-REFERENCE TO PRIOR APPLICATIONS

This application is a U.S. National Phase application under 35 U.S.C. § 371 of International Application No. PCT/EP2018/066610, filed on Jun. 21, 2018, and claims benefit to German Patent Application No. DE 10 2017 006 025.8, filed on Jun. 27, 2017. The International Application was published in German on Jan. 3, 2019 as WO 2019/002095 under PCT Article 21(2).

FIELD

The invention relates to a hydrogel-forming multicomponent fiber, to a textile fabric containing said multicomponent fiber, to a method for the production thereof and to the use thereof for medical applications.

BACKGROUND

Hydrogel-forming fibers are generally known. Accordingly, GB 2518199 describes a process for producing swellable fibers with at least one incorporated antimicrobial agent for wound care. In this case, a swellable, water-soluble polymer is deformed into swellable fibers with the incorporation of glycols (with 8 to 15 C atoms), glycerol, etc. by means of wet extrusion through nozzles. Metals (metal salts) are incorporated into the fibers as antimicrobial agents via the coagulation bath. The disadvantage of the process described is that the crosslinking with the metal salts contained in the spinning bath generates relatively brittle fibers which can only be processed into textile fabrics (woven, knitted, nonwoven, etc.) by using sufficient amounts of plasticizer (glycol, glycerol, etc.). Crosslinking is necessary in order to generate sufficient stability. It is further disadvantageous that the polymers change chemically upon dissolving and that plasticizers are required.

US 2008/0082065 A describes a composite fiber comprising carboxymethyl cellulose (CMC) (60 to 99%), a polygalactomannan or polyglucomannan (1 to 20%) and cellulose (short) fibers (in the simplest case: pulp fibers—2 to 15%) crosslinked by metal ions. Also described is a method for the preparation of said composite fiber, in which the CMC and the galacto- or glucomannan together with the pulp fibers are dispersed in water and then crosslinked with selected metal ions, the resulting gel is subsequently dissolved in a water-miscible solvent and deformed to form fibers, and these are then crosslinked again with a second crosslinking metal salt, wherein special, aqueous metal salt solutions based on Al, Ti, Bi, B or Zr compounds are used. The fibers are produced by stirring the water-miscible solvents. A disadvantage of the method described is that poorly-oriented and low-strength fibers with limited gelling capacity are obtained. Crosslinking is also necessary in this case in order to generate sufficient stability. It is further disadvantageous that the polymers change chemically upon dissolving and that metal ions are required.

US 2014/0322512 A1 describes core-sheath fibers composed of a hydrophobic, strength-giving core and a hydrophilic sheath polymer, a method for their production by means of electrospinning, and the use thereof in medical items. The sheath volume may vary between 100:1 to 1:1. The hydrophilic sheath polymer is crosslinked. The main disadvantage is the limited haptics of the surface-crosslinked fibers, the limited gel formation of the fiber surface, and the comparatively low mechanical strength of the fibers. A further disadvantage of the method is that electrospinning is a very expensive and hitherto less efficient forming process. In addition, the fiber geometry is limited to core-sheath fibers.

US 2005/0136253 A1 describes a deformation process for hydroxyl-containing polymer(s) (5 to 100% starch, starch derivatives, PVA, etc.) in selected dipolar protic and aprotic solvents or mixtures thereof by means of centrifugal nozzle/rotation spinning even at elevated temperatures. Also described are BiCo fiber structures (core-sheath, side-by-side and discontinuous statistical mixtures of both components). A disadvantage of this process are the limited mechanical stabilities and the low binding capacity for water or aqueous solutions, in particular for 0.9% aqueous sodium chloride solution. A further disadvantage is that the strength of the fibers obtained is relatively low. In addition, the selection of materials is limited to water-soluble polymers, wherein subsequent crosslinking is required.

Also known are carboxymethylated fibers, i.e. fibers produced by the subsequent carboxymethylation of viscose fibers (commercially available as "Aquacel fibers from Convatec; U.S. Pat. No. 6,547,30B; AU 757461 B; WO 00/01425 A1; EP 1,091,770 A1). Although these fibers allow a very high water absorption, they form a gel upon contact with water with complete loss of the fiber structure, which is undesirable for all possible applications.

Furthermore, viscose fibers with a proportion of carboxymethyl cellulose (CMC) are known. These are mixed fibers which are obtained by the spinning of carboxymethyl cellulose into the viscose textile pulp. Such fibers have also been manufactured commercially (U.S. Pat. Nos. 4,199,367 A, 4,289,824 A). A disadvantage of said mixed fibers is a lack of spinnability or limited fiber strength with high proportions of absorbent polymer. The water absorption capacity is also limited.

SUMMARY

In an embodiment, the present invention provides a hydrogel-forming multicomponent fiber, comprising: at least one first fiber component; and at least one second fiber component, wherein the first and the second fiber components are selected independently of one another from a group consisting of polysaccharides and/or polysaccharide derivatives, wherein the first fiber component is produced from a polysaccharide and/or a polysaccharide derivative having a water solubility of more than 50% by weight, and wherein the multicomponent fiber has a water solubility of less than 15% by weight.

BRIEF DESCRIPTION OF THE DRAWINGS

The present invention will be described in even greater detail below based on the exemplary figures. The invention is not limited to the exemplary embodiments. Other features and advantages of various embodiments of the present invention will become apparent by reading the following detailed description with reference to the attached drawings which illustrate the following.

DETAILED DESCRIPTION

In an embodiment, the present invention provides a hydrogel-forming fiber by means of which the above-described disadvantages can be at least partially eliminated. In particular, the fiber in contact with various liquids should form a transparent gel which is as homogeneous as possible and still retains its mechanical integrity.

In an embodiment, the present invention provides a hydrogel-forming multicomponent fiber comprising at least one first fiber component and at least one second fiber component, wherein the first and the second fiber components are selected independently of one another from the group of polysaccharides and/or polysaccharide derivatives, and wherein the first fiber component is produced from a polysaccharide and/or polysaccharide derivative having a water solubility of more than 50 wt %, preferably of more than 80 wt % and very particularly preferably of more than 95 wt %, and wherein the multicomponent fiber has a water solubility of less than 15 wt %.

Figure 1:
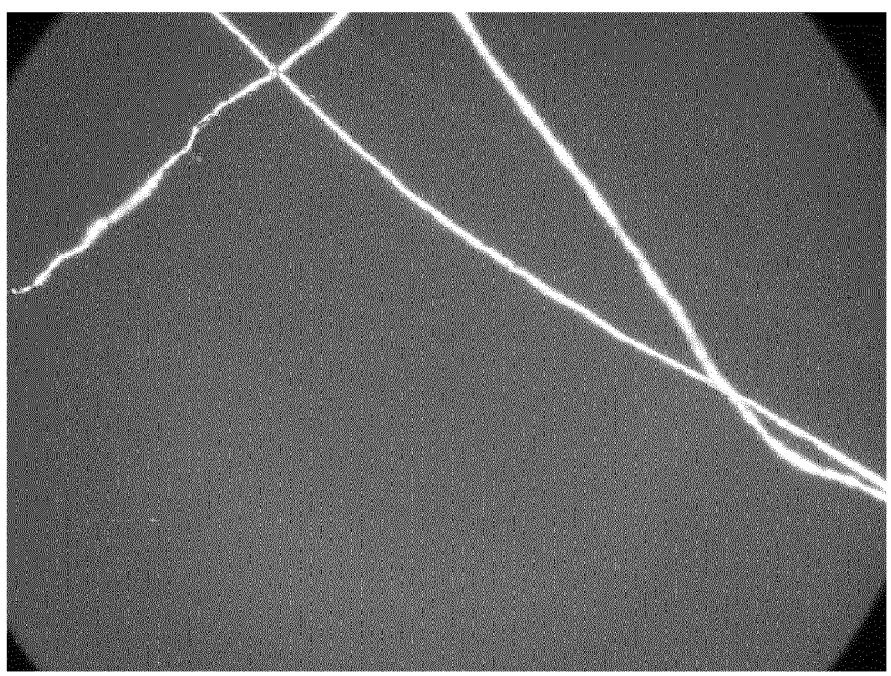
FIG. 1 shows the photographic image of three multicomponent fibers according to the invention in the dried state.
Figure 2:
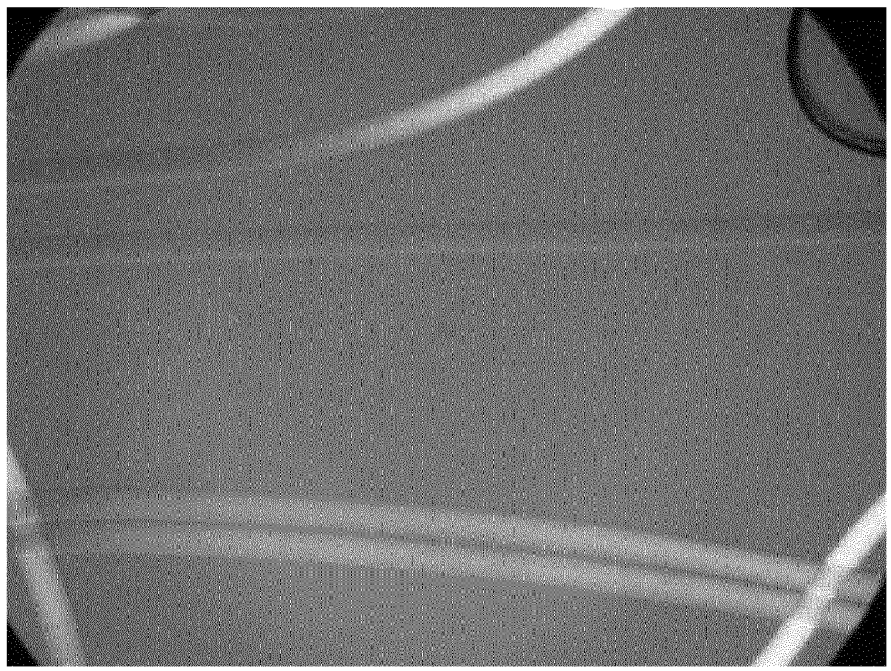
FIG. 2 shows the photographic image of several multicomponent fibers according to the invention in the swollen state. Swelling was effected by means of test solution A. It can clearly be seen that the fibers are swollen but without having lost their material cohesion, so that they still have a visually recognizable fiber form (fiber gel). In these fibers, the fiber components are arranged in a mixed phase.

The multicomponent fiber according to the invention is a hydrogel-forming multicomponent fiber. The term "hydrogel" is to be understood in the conventional sense as a water-containing but water-insoluble polymer whose molecules are linked chemically, for example by covalent or ionic bonds, or hydrogen bridges, or physically, for example by looping the polymer chains, to form a three-dimensional network. By means of incorporated hydrophilic polymer components, hydrogel-forming fibers swell in water and/or aqueous solutions with considerable increase in volume but without losing their material cohesion. A hydrogel-forming multicomponent fiber is therefore to be understood according to the invention as a fiber which forms a hydrogel at least with water and/or aqueous solutions, in particular 0.9% aqueous sodium chloride solution and/or test solution A (according to DIN EN 13726-01, section 3.2.2.3). In this case, the fiber swells in these solvents with an increase in volume without losing its material cohesion, so that it still has a visibly recognizable fiber form. In practical experiments, the multicomponent fiber according to the invention was found to form a homogeneous transparent "fiber gel" in test solution A, as demonstrated, for example, in FIG. 2. In this respect, the multicomponent fiber according to the invention can also be regarded as a multicomponent fiber forming a "fiber gel".

A feature of the multicomponent fiber according to the invention is therefore that it swells at least in water and/or aqueous solutions, in particular 0.9% aqueous sodium chloride solution and/or test solution A, with an increase in volume, for example with an expansion of the fiber diameter (20° C., test solution A, after 10 minutes) by more than 100%, for example from 100% to 600% and/or from 150% to 500% and/or from 200% to 400%.

A further feature of the multicomponent fiber according to the invention is that it does not lose its material cohesion upon swelling in water and/or aqueous solutions, in particular 0.9% aqueous sodium chloride solution, and/or test solution A, so that it still has a visually recognizable fiber form after swelling ("fiber gel").

A further feature of the multicomponent fiber according to the invention is that it has a water solubility of less than 15 wt %, for example from 0 wt % to 15 wt %, preferably of 0 wt % to 10 wt %, more preferably 0 wt % to 5 wt % and in particular of 0 wt % to 3 wt %. This is surprising since the first fiber component is produced starting from a water-soluble polysaccharide and/or polysaccharide derivative—all the more since it has been found that no chemical crosslinking of the multicomponent fiber via covalent and/or ionic bonds is necessary for setting the low water solubility, and is preferably not carried out. Advantageous in dispensing with chemical crosslinking is the fact that, when the fibers are used, for example in wound care, no foreign substances introduced by the crosslinking can be released.

Without committing to a mechanism according to the invention, it is assumed that the reduction in the water solubility of the multicomponent fiber compared to the first fiber component used as starting material is due to the fact that the first and second fiber components form a mixed phase and thereby stabilize each other. Such stabilization can take place particularly well if the mixed phase is designed such that the first and the second fiber components form entanglement and/or looping networks with one another. An entanglement and/or looping network is to be understood here as meaning a physical network which is formed by mutual penetration by macromolecules of the polysaccharide and polysaccharide derivatives at the phase boundary between the first and the second fiber component, so that the fiber components do not form clear phase boundaries. The fiber components are particularly preferably statistically distributed.

Such a mixed phase or such a entanglement or looping network can be obtained, for example, by preparing the hydrogel-forming multicomponent fiber from a spinning solution which is obtained by common dissolution of at least one first and one second polymer component, wherein the first and the second polymer component are selected independently of one another from the group of polysaccharides and/or polysaccharide derivatives, and wherein the first polymer component has a polysaccharide and/or polysaccharide derivative having a water solubility of more than 50 wt %.

The multi-component fiber forming the hydrogel according to the invention is distinguished by excellent mechanical properties, in particular tensile strength, elongation at break and good absorption capacity for test solution A. Thus, in a preferred embodiment of the invention, the multicomponent fiber according to the invention has a fineness-related tensile strength in a conditioned state of between 10 cN/tex and 40 cN/tex, more preferably between 15 cN/tex and 30 cN/tex, and/or a fineness-related elongation at break in a conditioned state of between 5% and 15%, more preferably between 5% and 10%, and/or an absorption capacity for test solution A between 5 g/g and 30 g/g, more preferably between 15 g/g and 30 g/g.

The multicomponent fiber according to the invention has at least two fiber components. These are preferably different in their chemical structure. As explained above, the two fiber components are preferably in the form of a mixed phase since such fibers can be produced particularly cost-effectively and simply, for example with the method according to the invention. The mixed phase can in this case be present in the fiber in a wide variety of arrangements. For example, it can be present as a component of a core-sheath arrangement, a segmented arrangement, in particular a segmented pie, side-by-side arrangement and/or island-in-the-sea arrangement. It is also preferably present as a component of a segmented pie or island-in-the-sea arrangement, since in these arrangements the components can swell freely.

In the case of a core-sheath arrangement, the mixed phase is preferably present in the sheath, since in this way a hydrogel-forming component of the fiber is present on the outside and can determine the character of the fiber. In the case of an island-in-the-sea arrangement, the hydrogel-forming component preferably represents the "sea".

According to the invention, the mixed phase particularly preferably forms the main component of the fiber. Thus, the fiber preferably consists of more than 90 wt %, more preferably of from 95% by weight to 95 wt % of the mixing phase.

In a further preferred embodiment of the invention, the hydrogel-forming multicomponent fiber in the dry state has a proportion of polysaccharides and/or polysaccharide derivatives of more than 95 wt %, more preferably of more than 97 wt %, in particular of more than 99 wt %, based in each case on the total weight of the multicomponent fiber.

In the dry state, the multicomponent fiber according to the invention preferably has a fiber diameter between 10 μm and 100 μm. In a preferred embodiment of the invention, the fiber diameter is in the range between 10 μm and 50 μm, more preferably between 10 μm and 25 μm.

The ratio of the first and second fiber components is preferably between 80:20 and 10:90, more preferably between 70:30 and 20:80, and most preferably between 65:35 and 50:50.

According to the invention, the first fiber component is selected from the group of polysaccharides and/or polysaccharide derivatives, wherein the first fiber component is produced from a polysaccharide and/or polysaccharide derivative having a water solubility of more than 50 wt %.

According to the invention, the first fiber component is particularly preferably selected from the group of cellulose derivatives, for example ionic or nonionic cellulose ethers, in particular carboxymethyl cellulose and/or hydroxypropyl cellulose. Particularly suitable polysaccharide derivatives for the first fiber component according to the invention are carboxyalkyl cellulose, in particular carboxymethyl cellulose, hydroxyalkyl cellulose, in particular hydroxypropyl cellulose and/or sulfoalkyl cellulose. The advantage thereof is their good solubility in protic solvents, preferably in water.

According to the invention, the second fiber component is likewise selected from the class of polysaccharides and/or polysaccharide derivatives, wherein polysaccharides are preferred because of their lower solubility compared to polysaccharide derivatives. The second fiber component is preferably produced from a polysaccharide and/or polysaccharide derivative having a water solubility of 0 wt %. to 5 wt %, and particularly preferably having a water solubility of 0 wt % to 1 wt %.

The polysaccharides of the second fiber component can be ionic or preferably nonionic polysaccharides, particularly preferably cellulose.

In principle, the multicomponent fiber can have a very wide variety of combinations of first and second fiber components. It is advantageous here if the two fiber components can be dissolved together in a solvent, as explained below. Combinations of ionic or nonionic cellulose ethers, in particular carboxymethyl cellulose and/or hydroxypropyl cellulose as the first fiber component with cellulose as the second fiber component, are preferred.

In a further preferred embodiment of the invention, the multicomponent fibers are staple fibers which preferably have a dry-state fiber length of from 1 mm to 60 mm, more preferably from 3 mm to 40 mm. These are particularly suitable for processing into staple fiber nonwovens.

The hydrogel-forming multicomponent fiber can be processed into textile fabrics using conventional methods. A further object of the present invention is therefore a textile fabric, for example a woven fabric, knitted fabric, crocheted fabric and/or a nonwoven fabric, in particular a staple fiber nonwoven, which comprises the hydrogel-forming multicomponent fiber according to the invention and preferably consists of more than 80 wt %, more preferably more than 90 wt %, and in particular more than 95 wt % hydrogel-forming multicomponent fibers according to the invention.

The multicomponent fiber according to the invention is extremely well suited for producing materials for medical applications, in particular for producing wound pads, wound dressings, suture materials, implants, tissue engineering scaffolds, medicaments, carrier materials, hygiene products, in particular sanitary hygiene products, diapers and incontinence products, and/or cosmetic products.

The present invention also relates to a method for the preparation of a hydrogel-forming multicomponent fiber having a water solubility of less than 15 wt %, comprising the following steps:

Preparing at least one spinning solution by the common dissolution in a solvent of at least one first polymer component and at least one second polymer component, wherein the first and second polymer components are selected independently of one another from the group of polysaccharides and/or polysaccharide derivatives, and wherein the first polymer component has a water solubility of more than 50 wt %, preferably of more than 80 wt % and very particularly preferably of more than 95 wt %;

Feeding the spinning solution to a spinneret and extruding the spinning solution through the spinneret into an air gap to produce a multicomponent structure;

Introducing the multicomponent structure into a precipitation bath to form the multicomponent fiber;

Removing the solvent in at least one washing bath and

Drying the multicomponent fiber.

Preferably, a multicomponent fiber according to the invention as described here can be produced with the method according to the invention.

A substantial feature of the method according to the invention is that, in a first method step, a spinning solution is produced by common dissolution in a solvent of at least one first and at least one second polymer component, wherein the first and the second polymer components are selected independently of one another from the group of polysaccharides and/or polysaccharide derivatives, and wherein the first polymer component has a water solubility of more than 50 wt %.

Without committing to a mechanism according to the invention, it is assumed that the common dissolution of the first and second fiber components leads to a mutual penetration and to the formation of a mixed phase or of entanglement or looping networks between the fiber components in the multicomponent fiber according to the invention.

This surprisingly results in a significant reduction in the water solubility of the multicomponent fiber compared with the water-soluble polysaccharides and/or polysaccharide derivatives used as starting materials, which leads to the advantages described above.

In particular, it is surprising that the low water solubility of the multicomponent fiber can also be achieved without chemical modification of the polymer components. Cross-linking, in particular by chemical crosslinkers, of the first polymer component can thus be dispensed with. Furthermore, a fiber in which the fiber components have an arrangement in mixed phases can be produced particularly well by the common dissolution.

Furthermore, it is possible to adjust the quantitative ratios between the first and the second polymer component very precisely. Said ratios are preferably between 80:20 and 10:90, more preferably between 70:30 and 20:80, and very particularly preferably between 65:35 and 50:50.

By varying the polymer fractions and/or specifically selecting the polymer components in the spinning solution, the fiber properties can be adjusted in a simple manner, for example the moisture absorption capacity and the textile-physical properties.

In a preferred embodiment of the invention, the dissolution of the first and the second polymer components takes place in the form of a direct dissolution. Direct dissolution is a known method and is described, for example, in T. Roder, R. Möslinger, U. Mais, B. Morgenstern, U. Glatter "Charakterisierung der Lösungsstrukturen in technisch relevanten Celluloselösungen", Lenzinger Berichte 82 (2003) 118-127, in R. Maron, Ch. Michels, E. Taeger, "Investigations for preparation of cellulose Solutions in NMMO and the following forming", Lenzinger Berichte 74 (1994), 27-29, or in D. Cole, A. Jones, "Solvent-Spun Fibre—A New Member of the Cellulose Fibre Family", Lenzinger Berichte 69 (1990), 73-77.

The most varied solvents, which preferably allow direct dissolution of the first polymer component and/or of the second polymer components, can be used as solvents. Particularly suitable for this purpose are N-methyl morpholine N-oxide monohydrate, but also ionic liquids such as, for example, EMIMAc and BMIMCI.

In a further method step, the spinning solution is fed to a spinneret, and the spinning solution is extruded through the spinneret into an air gap. A single or multi-component spinneret can be used as spinneret. The extruded multicomponent structure is drawn in the air gap.

In a further method step, the multicomponent structure is introduced into a precipitation bath to form the multicomponent fiber. The precipitation bath serves for simultaneous regeneration/coagulation of the multicomponent structure to form the multicomponent fiber according to the invention. The precipitation bath preferably contains aqueous salt solutions or organically aqueous solutions of the solvent used for dissolving the polymer components. The aqueous salt solutions preferably comprise sulfates, in particular sodium sulfate and zinc sulfate. The salt content of the precipitation bath is preferably up to 20 wt %, more preferably 1 to 10 wt %, and in particular 1 to 5 wt %. The ratio between the solvent and water used to dissolve the polymer components is preferably between 15:85 and 35:65.

In a further method step, the solvent is removed in at least one washing bath. The at least one washing bath preferably contains water, the solvent used to dissolve the polymer components, an organic solvent such as alcohol, acetone and/or mixtures thereof. In a preferred embodiment, a plurality of washing baths are used which have a different content of organic solvent. By using organic solvents which do not dissolve the first and/or second polymer component, the multicomponent fiber can be stabilized.

Drying of the multicomponent fiber takes place in a further method step.

The method according to the invention is distinguished in that it is technically and technologically simple to carry out and can be scaled up in a simple manner. As explained above, hydrogel-forming multicomponent fibers having high mechanical integrity, in particular in the moist and/or swollen state, can be obtained by the method according to the invention.

Furthermore, with the method according to the invention, the multicomponent fiber according to the invention can be produced in a simple manner, for example in an arrangement in macroscopic mixing phases, since it is already preformed by the solution preparation.

Optionally, the multicomponent fibers can be cut to the desired staple length (preferably 1 to 60 mm). Usual post-treatment steps such as bleaching, brightening or crimping may be used.

In the following, the methods are listed that are used to determine the measurement methods used in this invention:
Water Solubility of the Polysaccharide and/or Polysaccharide Derivative:

The water solubility is determined using in-house specifications. About 2 g of the polysaccharide or polysaccharide derivative, whose dry content (TG in %) was determined in a separate sample at 105° C., is weighed out with analytical precision (weight of PS in g), 100 ml of deionized water is added, and the sample is stirred for 30 min at room temperature. The sample is then passed through a G3 frit, which was dried and weighed beforehand at 105° C. (A in g), filtered, and the filter cake is dried to a constant weight with frit at 105° C. and weighed (B in g). The water solubility of the polysaccharide or polysaccharide derivative results from:

$$\text{Water solubility of the polysaccharide (derivative)s } [\%] = \left(1 - \frac{B-A}{PS \times TG/100}\right) \times 100$$

Water Solubility of the Multicomponent Fiber:

The water solubility is determined using in-house specifications. About 2 g of the multicomponent fiber, whose dry content (TG in %) was determined in a separate sample at 105° C., is weighed out with analytical precision (weight of F in g), mixed with 100 ml of deionized water and the sample is stirred for 30 min at room temperature. The fiber is then passed through a G3 frit, which was dried and weighed beforehand at 105° C. (A in g), filtered, the fiber is dried to constant weight with frit at 105° C. and weighed (B in g). The water solubility of the multicomponent fiber results from:

$$\text{Water solubility water of the multicomponent fiber } [\%] = \left(1 - \frac{B-A}{F \times TG/100}\right) \times 100$$

Fiber Diameter

The fiber diameter of the dried or swollen multicomponent fibers was determined by measuring using a microscope.

Fineness-Related Tensile Strength and Elongation at Break in the Conditioned State:

The fineness-related tensile strength and elongation at break in the conditioned state are determined by DIN EN ISO 5079.

Fiber Fineness:

The fiber fineness is determined by DIN EN ISO 1973.

Absorption Capacity for Blood Substitute Liquid (Test Solution A):

The absorption capacity for blood substitute liquid is determined on the basis of DIN 53923. Instead of the absorption of water described in DIN 53923, the absorption of test solution A is determined.

Test Solution a According to DIN EN 13726-01, Section 3.2.2.3

Test solution A containing sodium chloride and calcium chloride solution with a content of 142 mmol sodium ions and 2.5 mmol calcium ions as chlorides has an ion composition comparable to the human serum or wound secretion. It is prepared by dissolving 8.298 g sodium chloride and 0.368 g calcium chloride dihydrate in deionized water and filling to 1 l in a measuring flask.

The invention is explained in more detail below with reference to an example:

Example: Preparation of a Multicomponent Fiber from Sodium Carboxymethyl Cellulose According to the Invention as a First Polymer Component and from Cellulose as a Second Polymer Component in a Ratio of 50/50

17.47 g cellulose (*eucalyptus* sulfite pulp, Cuoxam DP: 500, dry content (TG): 93%) (second polymer component) are applied to the single fiber by means of Ultra Turrax in water and pressed to a dry content of 35%. 17.66 g Na-CMC (DS: 0.9, MW: 250,000, TG: 92%) (first polymer component) are stirred by means of Ultra Turrax into 377 g of 50% N-methylmorpholine N-oxide (NMMO) containing 0.16 g propyl gallate as stabilizer and converted together into a homogeneous suspension after addition of the pressed-out pulp. This suspension is transferred to a laboratory kneader and converted under shearing, temperature and vacuum by removing the excess water up to the NMMO monohydrate into a homogeneously distributed blend polymer solution having a zero shear viscosity of 6000 Pas at 85° C. By means of a dry wet spinning process, the blend polymer solution is deformed into multicomponent fibers having a fineness of 1.64 dtex with the listed fiber properties using the following spinning conditions:

| Spinning conditions: | | |
|---|---|---|
| Textile pulp temperature | ° C. | 79 |
| Nozzle orifice diameter | μm | 100 |
| Number of capillaries | | 30 |
| Spinning pressure | bar | 30 |
| Air gap | mm | 40 |
| Precipitation bath | | 5% Na$_2$SO$_4$ |
| Spinning speed | m/min | 30 |
| Washing baths | | Water/Ethanol 75/25, 50/50, 25/75 |
| Fiber testing: | | |
| Fineness | dtex | 1.77 |
| Fineness-related tensile strength, cond. | cN/tex | 24.5 |
| Elongation at break, cond. | % | 8.2 |
| Absorption capacity Test solution A | g/g | 21.4 |

It was found that the hydrogel-forming multicomponent fiber according to the invention has excellent fineness-related tensile strength and elongation at break, and excellent absorption capacity for test solution A.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A hydrogel-forming multicomponent fiber, comprising:
   at least one first fiber component; and
   at least one second fiber component,
   wherein the first fiber component is produced from a first polymer component comprising at least one ionic cellulose ether, nonionic cellulose ether, or a combination thereof having a water solubility of more than 50% by weight,
   wherein the second fiber component is produced from a second polymer component comprising cellulose,
   wherein the first and the second fiber components are present as a mixed phase wherein the first and the second fiber components form entanglement networks, looping networks, or a combination thereof with one another, and
   wherein the multicomponent fiber has a water solubility of less than 15% by weight.

2. The hydrogel-forming multicomponent fiber according to claim 1, wherein the hydrogel-forming multicomponent fiber does not have a chemical crosslinking of the first and/or second fiber component via covalent and/or ionic bonds.

3. The hydrogel-forming multicomponent fiber according to claim 1, wherein the hydrogel-forming multicomponent fiber swells in at least one of a 0.9% aqueous sodium chloride solution and a test solution A comprising 142 mmol sodium ions and 2.5 mmol calcium ions, according to DIN EN 13726-01, section 3.2.2.3, by more than 100% with expansion of a fiber diameter.

4. The hydrogel-forming multicomponent fiber according to claim 1, wherein the mixed phase is present as a component of a core-sheath arrangement, a segmented arrangement comprising a segmented pie, a side-by-side arrangement, an island-in-the-sea arrangement, or a combination thereof.

5. The hydrogel-forming multicomponent fiber according to claim 1, wherein the hydrogel-forming multicomponent fiber is obtained by common dissolution of the at least one first polymer component and the at least one second polymer component.

6. The hydrogel-forming multicomponent fiber according to claim 1, wherein the hydrogel-forming multicomponent fiber has a fineness-related tensile strength in a conditioned state, according to DIN EN ISO 5079, of between 10 cN/tex and 40 cN/tex, and/or a fineness-related elongation at break in the conditioned state, according to DIN EN ISO 5079, of between 5% and 15%, and/or an absorption capacity for test solution A comprising 142 mmol sodium ions and 2.5 mmol calcium ions, according to DIN EN 13726-01, section 3.2.2.3, of between 5 g/g and 30 g/g.

7. The hydrogel-forming multicomponent fiber according to claim 1, wherein a ratio of first and second fiber components is between 80:20 and 10:90.

8. The hydrogel-forming multicomponent fiber according to claim 1, wherein the second polymer component comprises cellulose having a water solubility of 0 wt % to 5 wt %.

9. The hydrogel-forming multicomponent fiber according to claim 1, wherein the first fiber component is produced from a first polymer component comprising carboxymethyl cellulose, hydroxypropyl cellulose, sulfoalkyl cellulose, or a combination thereof.

10. A textile fabric, comprising:
the hydrogel-forming multicomponent fiber according to claim 1,
wherein the textile fabric comprises at least one of woven fabric, knitted fabric, crocheted fabric, and non-woven fabric.

11. A medical material comprising:
at least one hydrogel-forming multicomponent fiber according to claim 1 and a textile fabric comprising said hydrogel-forming multicomponent fiber,
wherein the medical material is at least one of wound pads, wound dressings, suture materials, implants, tissue engineering scaffolds, medicaments, carrier materials, sanitary hygiene products, and cosmetic products.

12. A method for preparation of a hydrogel-forming multicomponent fiber having a water solubility of less than 15% by weight, comprising the following steps:
preparing at least one spinning solution by a common dissolution in a solvent of at least one first polymer component and at least one second polymer component, wherein the first polymer component comprises at least one ionic cellulose ether, nonionic cellulose ether, or a combination thereof and has a water solubility of more than 50% by weight, and wherein the second polymer component comprises cellulose,
feeding the at least one spinning solution to a spinneret and extruding the at least one spinning solution through the spinneret into an air gap to produce a multicomponent structure;
introducing the multicomponent structure into a precipitation bath to form the multicomponent fiber;
removing the solvent in at least one washing bath; and
drying the multicomponent fiber.

13. The method according to 12, wherein no chemical crosslinking of the first and/or second fiber component via covalent and/or ionic bonds is carried out.

14. The method according to claim 12, wherein the solvent comprises N-methyl morpholine N-oxide monohydrate, ionic liquids, or a combination thereof.

15. The hydrogel-forming multicomponent fiber according to claim 1, wherein the first fiber component is produced from a first polymer component comprising at least one ionic cellulose ether, nonionic cellulose ether, or a combination comprising at least one ionic cellulose ether, nonionic cellulose ether, or a combination thereof having a water solubility of more than 90% by weight.

16. The hydrogel-forming multicomponent fiber according to claim 15, wherein the first fiber component is produced from a first polymer component comprising at least one ionic cellulose ether, nonionic cellulose ether, or a combination thereof having a water solubility of more than 95% by weight.

17. The hydrogel-forming multicomponent fiber according to claim 1, wherein the entanglement network, looping network, or a combination thereof are present as a component of a core-sheath arrangement, a segmented arrangement comprising a segmented pie, a side-by-side arrangement, an islant-in-the-sea arrangement, or a combination thereof.

18. The method of claim 12, wherein the first polymer component has a water solubility of more than 80 wt %.

* * * * *